US010219699B2

(12) United States Patent
Wilder et al.

(10) Patent No.: US 10,219,699 B2
(45) Date of Patent: Mar. 5, 2019

(54) IMPLANTABLE SENSORS AND METHODS OF USE

(71) Applicant: Intellirod Spine, Inc., Akron, OH (US)

(72) Inventors: Steven E. Wilder, Ashland, OH (US); Daniel J. Johnson, Cleveland, OH (US); Richard R. Navarro, Hinckley, OH (US)

(73) Assignee: Intellirod Spine Inc., Akron, OH (US)

( * ) Notice: Subject to any disclaimer, the term of this patent is extended or adjusted under 35 U.S.C. 154(b) by 885 days.

(21) Appl. No.: 14/537,398

(22) Filed: Nov. 10, 2014

(65) Prior Publication Data
US 2016/0128573 A1    May 12, 2016

(51) Int. Cl.
*A61B 5/00*    (2006.01)
*A61B 90/00*    (2016.01)
(Continued)

(52) U.S. Cl.
CPC .......... *A61B 5/0031* (2013.01); *A61B 5/0015* (2013.01); *A61B 5/0024* (2013.01); *A61B 5/4566* (2013.01); *A61F 2/4657* (2013.01); *A61B 5/4851* (2013.01); *A61B 17/7002* (2013.01); *A61B 2090/064* (2016.02);
(Continued)

(58) Field of Classification Search
CPC ... A61B 5/0015; A61B 5/0024; A61B 5/0031; A61B 5/4566; A61B 5/4851; A61B 17/7002; A61B 2090/064; A61B 2562/0261; A61F 2/4657; A61F 2002/4666
See application file for complete search history.

(56) References Cited

U.S. PATENT DOCUMENTS

| 5,179,942 A | 1/1993 | Drulias et al. |
| 5,709,685 A * | 1/1998 | Dombrowski ..... A61B 17/7037 24/336 |

(Continued)

FOREIGN PATENT DOCUMENTS

| WO | 2009130577 | 10/2009 |
| WO | 20160076838 | 5/2016 |

OTHER PUBLICATIONS

European Patent Office, International Search Report and Written Opinion for PCT/ dated Jun. 11, 2015, 18 pages, Rijswijk Netherlands.

*Primary Examiner* — Devin B Henson
(74) *Attorney, Agent, or Firm* — Middleton Reutlinger

(57) ABSTRACT

Systems, methods, and apparatus are described herein for obtaining medical diagnostic measurements from implanted sensors. In various embodiments, a spinal implant-monitoring apparatus may include: a bridge defining a first hermetically-sealed interior and two or more legs; one or more strain gauges contained within the first hermetically-sealed interior of the bridge to provide a signal indicative of strain measured between the legs of the bridge; a housing defining a second hermetically-sealed interior, the housing mounted on a surface of the bridge; and control circuitry contained within the second hermetically-sealed interior. The control circuitry may be in communication with the one or more strain gauges and may be configured to convert the signal into digital data representative of the signal. Methods of using such apparatus are also disclosed.

15 Claims, 10 Drawing Sheets

(51) Int. Cl.
  *A61B 17/70* (2006.01)
  *A61F 2/46* (2006.01)
  *H04W 84/18* (2009.01)

(52) U.S. Cl.
  CPC ........... *A61B 2562/0261* (2013.01); *A61F 2002/4666* (2013.01); *H04W 84/18* (2013.01)

(56) References Cited

U.S. PATENT DOCUMENTS

| | | | |
|---|---|---|---|
| 6,083,248 A | 7/2000 | Thompson | |
| 6,341,504 B1 | 1/2002 | Istook | |
| 7,357,037 B2* | 4/2008 | Hnat | A61B 5/0031 |
| | | | 73/795 |
| 7,632,216 B2 | 12/2009 | Rahman et al. | |
| 8,073,548 B2 | 12/2011 | Colvin, Jr. et al. | |
| 9,113,485 B2* | 8/2015 | Chintalapudi | H04W 74/0841 |
| 2004/0011137 A1 | 1/2004 | Hnat et al. | |
| 2006/0058790 A1* | 3/2006 | Carl | A61B 17/70 |
| | | | 606/248 |
| 2006/0069436 A1 | 3/2006 | Sutton et al. | |
| 2009/0275867 A1 | 11/2009 | Santos-Manne et al. | |
| 2010/0060431 A1* | 3/2010 | Stevenson | A61B 5/0031 |
| | | | 340/10.1 |
| 2010/0094302 A1* | 4/2010 | Pool | A61B 17/7004 |
| | | | 606/90 |
| 2011/0125063 A1 | 5/2011 | Shalon et al. | |
| 2011/0195666 A1 | 8/2011 | Forsell | |
| 2012/0071793 A1 | 3/2012 | Gal et al. | |
| 2012/0123232 A1 | 5/2012 | Najarian et al. | |
| 2012/0184826 A1 | 7/2012 | Keenan et al. | |
| 2012/0247227 A1* | 10/2012 | Crivelli | G01L 19/086 |
| | | | 73/862.381 |
| 2013/0079693 A1 | 3/2013 | Ranky et al. | |
| 2013/0226034 A1 | 8/2013 | Stein et al. | |
| 2014/0046403 A1 | 2/2014 | Aghassian | |
| 2014/0062717 A1 | 3/2014 | Mudumbai et al. | |
| 2014/0066814 A1 | 3/2014 | Gupta et al. | |
| 2017/0196508 A1* | 7/2017 | Hunter | A61B 5/4851 |

* cited by examiner

IMPLANTABLE SENSORS AND METHODS OF USE

BACKGROUND

Implanted sensors may measure, and make available to other devices using wireless technology, various medical diagnostic measurements such as strain readings, e.g., from body segments or joints in between. Often such measurements are obtained while visiting a doctor's office or during surgery. A doctor may bring a device with a wireless reader (e.g., NFC, RFID, BlueTooth, etc.) into wireless range of one or more implanted sensors, e.g., in the patient's back, to wirelessly obtain medical diagnostic data from those sensors, e.g., during a routine visit or during surgery.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of embodiments of the invention.

DETAILED DESCRIPTION

Figure 1:
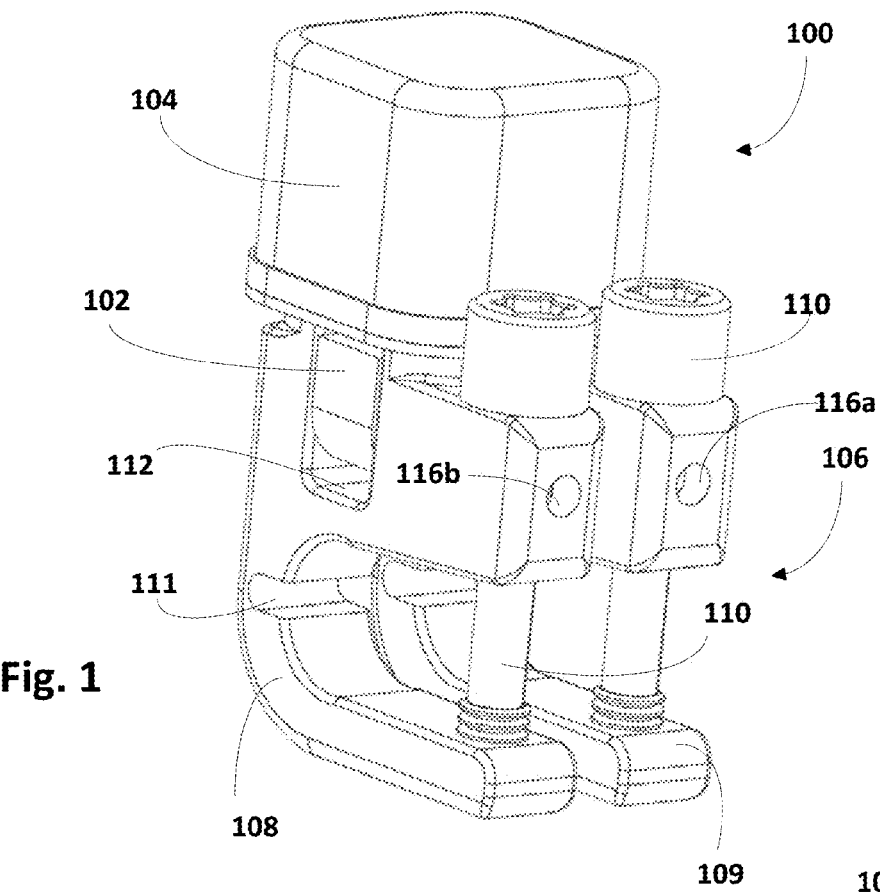
FIG. 1 is a perspective view of an implantable sensor, in accordance with various embodiments.
Figure 2:
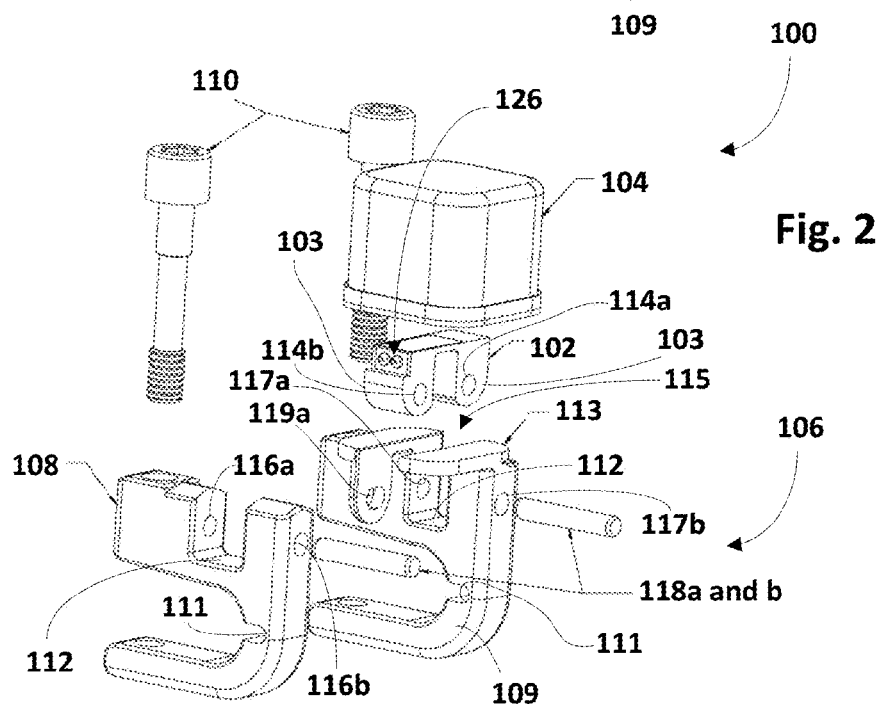
FIG. 2 is an exploded view of the implantable sensor of FIG. 1, in accordance with various embodiments.
Figure 3:
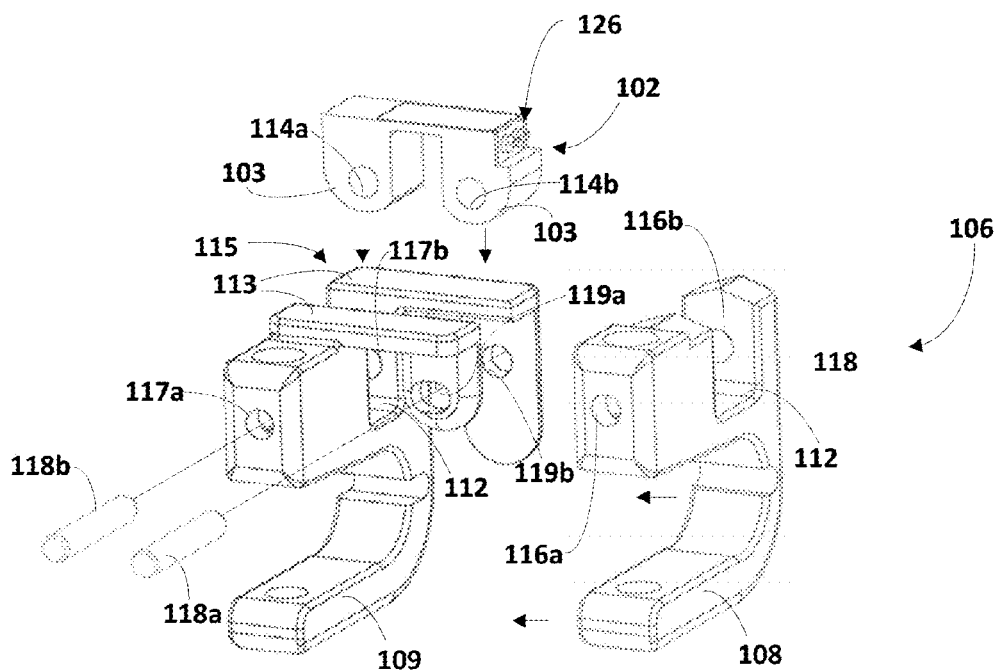
FIG. 3 is an exploded view of a clamp assembly and a bridge of the implantable sensor of FIGS. 1 and 2, in accordance with various embodiments.

Referring to FIGS. 1-3, an implant-monitoring apparatus 100 (also referred to as an "implantable sensor" or "implanted sensor" if already implanted in/on a patient) may include a bridge 102 and a separate housing 104 mounted adjacent a surface of bridge 102. Bridge 102 may define one or more legs 103 (see FIGS. 2-3), and may house various circuitry configured, e.g., to obtain various types of medical diagnostic data, such as strain measured between legs 103 of bridge. "Medical diagnostic data" may include but is not limited to strain readings, e.g., from a spinal fusion rod implanted parallel to a patient's spine to facilitate spinal fusion, accelerometer readings (e.g., to determine physical activity engaged in by a patient), and so forth. Housing 104 may also house various circuitry, such as circuitry to wirelessly communicate with, e.g., wireless readers operated by medical personnel.

As used herein, a "wireless reader" may refer to a computing device, hand-held or otherwise, that is configured to communication wirelessly with implanted sensors. In some embodiments, the wireless reader may be a proprietary device designed specifically for use with implanted sensors. In other embodiments, the wireless reader may be mobile computing device such as a smart phone, tablet computer, or wearable computing device (e.g., smart glasses, smart watch) that is programed (e.g., by downloading an "app") to communication wirelessly with implanted sensors.

Bridge 102 may be disposed between housing 104 and a clamping apparatus 106. Clamping apparatus 106 may be configured to be secured to various body parts and/or implants, such as spinal fusion rods implanted parallel to a patient's spine. In various embodiments, clamping apparatus 106 may include two or more clamps, such as a first clamp 108 and a second clamp 109, that may be loosened or tightened in various ways, such as by manipulating one or more screws 110. In various embodiments, clamps 108 and 109 may include hinge recesses 111 that may provide clamps 108 and 109 with some additional freedom of movement.

As shown best in FIGS. 2-3, first clamp 108 and second clamp 109 each may include a recess 112 into which a leg 103 of bridge 102 may be inserted. Bridge 102 may include apertures 114a and 114b, e.g., through legs 103. First clamp 108 may include apertures 116a and 116b. Second clamp 109 may include apertures 117a and 117b. Second clamp 109 may also include an isolation structure 115 that may be used to isolate strain sensed by bridge 102 from other forces that may be imparted on apparatus 100, e.g., by muscles or other adjacent tissue. In various embodiments, isolation structure 115 may define a platform 113 on which housing 104 may be mounted, though this is not required. In various embodiments, strain isolation structure 115 may define one or more strain isolation apertures 119a and 119b (shown best in FIG. 3).

Bridge 102 and clamping apparatus 106 may be attached to each other in various ways. As seen best in FIG. 3, insertion of bridge 102 into recess 112 may align aperture 114a of bridge 102 with apertures 117a and 117b of second clamp 109. Insertion of bridge 102 into recess 112 may also align aperture 114b of bridge 102 with apertures 116a and 116b of first clamp 108, as well as with strain isolation apertures 119a and 119b. Once these multiple apertures are aligned, a first pin 118a may be inserted through aperture 116a, through strain isolation aperture 119a, through aperture 116b, and into strain isolation aperture 119b. A second pin 118b likewise may be inserted through apertures 117a and 114a, and into aperture 117b.

When assembled as described above, strain isolation structure 115 may secure first clamp 108 and second clamp 109 together. Additionally, bridge 102 may be isolated from forces imparted by nearby muscle or tissue by mounting housing 104 on platform 113, rather than directly on bridge 102. Accordingly, mechanical forces sensed by bridge 102 may be limited to strain sensed between legs 103 of bridge 102.

In some embodiments, first clamp 108 and second clamp 109 may be rigidly secured to a rod implanted in a patient's body, e.g., parallel to the patient's spine, such as a spinal fusion rod. Such a rod may be curved or straight. Any displacement of or any forces imparted on the rod subsequent to the clamps 108 and 109 being secured to it may be mechanically transferred and/or amplified by the clamps 108 and 109 into strain between legs 103 of bridge 102. Bridge 102 may include various circuitry that is configured to sense this strain in various ways.

Figure 4:
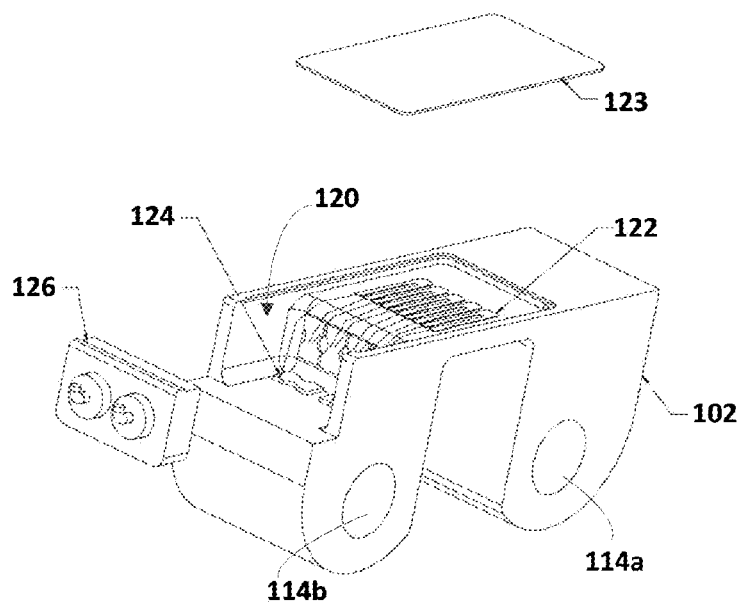
FIG. 4 is an exploded view of a bridge of an implantable sensor, in accordance with various embodiments.

For instance, in the embodiment shown in FIG. 4, bridge 102 defines a first hermetically-sealed interior 120. One or more strain gauges 122 may be housed within first hermetically-sealed interior 120. Strain gauges 122 may provide one or more signals indicative of strain measured between legs 103. In some embodiments, strain gauges 122 may measure strain between legs 103 of bridge 102 and/or elsewhere on bridge 102, such as on one or more surfaces of bridge 102.

In various embodiments, at least one of one or more strain gauges 122 may be connected to an adjacent strain gauge by a solder tab 124. In various embodiments, one or more strain gauges 122 may include a plurality of strain gauges connected in series to from a series of strain gauges. In some embodiments, terminal ends of the series of strain gauges 122 may be coupled with feed-through pins 126 that pass from within first hermetically-sealed interior 120 to a position exterior from bridge 102. In various embodiments, feed-through pins 126 may pass through housing 104 into another hermetically-sealed interior of housing 104 to couple the series of strain gauges 122 with control circuitry contained therein. In some embodiments, bridge 102 may include a cover 123, which in some embodiments may be constructed with titanium foil.

In embodiments where apparatus 100 is securable to a spinal fusion rod implanted in a patient's body, changes in geometry of bridge 102 and how it is mounted may be used to adjust a percentage of strain that is transferred into bridge 102 to be measured by one or more strain gauges 122. In various embodiments, strain transferred by bridge 102 to one or more strain gauges 122 may be directly proportional to any change in a distance between axes of pins 118*a* and 118*b*, a height of a center of pins 118*a* and 118*b* from a center of the spinal rod, and/or a thickness/width of the portion of bridge 102 in which one or more strain gauges 122 are mounted. In various embodiments, strain transferred by bridge 102 to one or more strain gauges 122 may be inversely proportional to any change in the span length of bridge 102, as well as a distance from centers of axes of pins 118*a* and 118*b* to a central plane of bridge 102, otherwise referred to as an "offset" of bridge 102.

In some embodiments, the surface of bridge 102 that is up top in FIGS. 2-4 may have a first width, and an opposite surface (i.e., including legs 103) may have a second width that is less than the first width, e.g., to assist in driving the mechanical behavior of bridge 102. In some embodiments, a stress concentration zone (not depicted) may be selectively incorporated somewhere on a surface of bridge 102, e.g., at one end of bridge 102 along its longitudinal axis. If sufficient force is imparted on bridge 102 to break it, the break may occur at this zone, rather than at another location that might result in cross contamination between electronic components contained in interior 120 and the biological environment in which apparatus 100 is implanted. In other embodiments, no stress concentration zone may be included.

Figure 5:
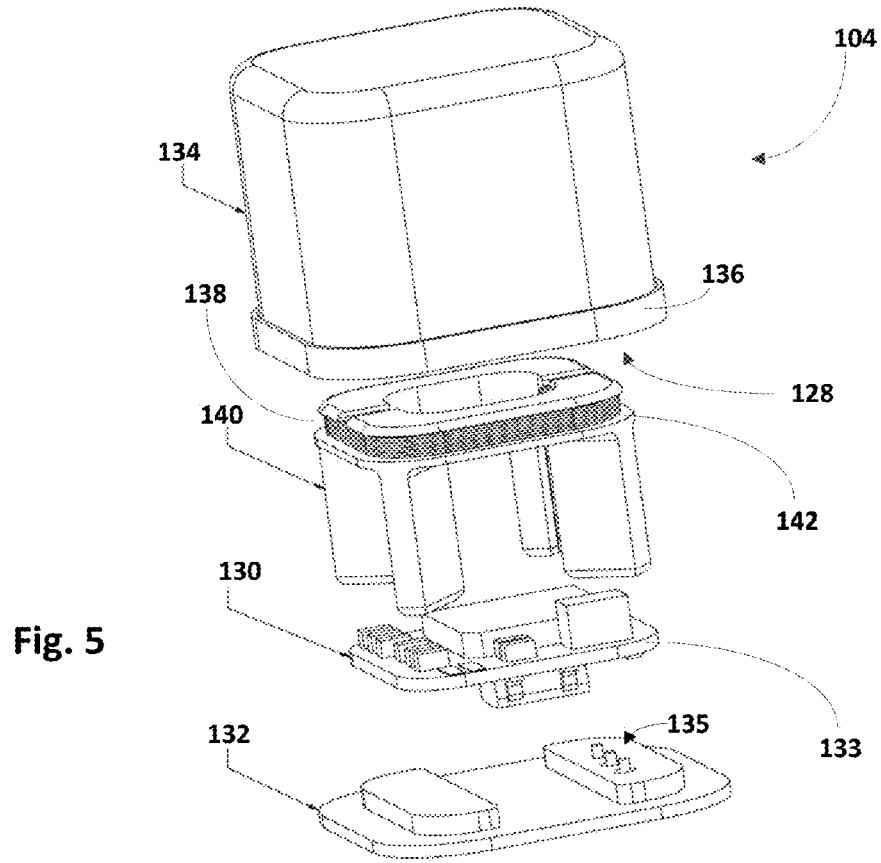
FIG. 5 is an exploded view of control circuitry contained in a housing that may form part of an implantable sensor, in accordance with various embodiments.

Referring to FIG. 5, housing 104 may define a second hermetically-sealed interior 128 to contain control circuitry 130. In various embodiments, housing 104 may include a generally-planar lid 132 mounted on a ceramic cap 134. In some embodiments, ceramic cap 134 may be coated with various materials, such as gold, e.g., using vapor coating. In some embodiments, a portion of ceramic cap 134 adjacent the generally-planar lid 132 may be encompassed by a metal ring 136. In some embodiments, metal ring 136 may be a titanium ring that may be brazed onto ceramic cap 134, which may be coated with gold or other materials. Metal ring 136 also may be welded or otherwise bonded to a corresponding metal portion (not depicted) of generally-planar lid 132.

In various embodiments, control circuitry 130 may be contained on a printed circuit board 133 that is mounted on generally-planar lid 132, though this is not required. In various embodiments, control circuitry 130 may be communicatively coupled with contacts 135 (e.g., one positive, one negative, one ground), which may be constructed from various materials, such as platinum. Control circuitry 130 may come in various forms, including but not limited to a field-programmable gate array ("FPGA"), an application-specific integrated circuit ("ASIC"), one or more processors configured to execute instructions stored in memory, and so forth. In some embodiments where a FPGA is employed, control circuitry 130 may be created in hardware description languages such as VHDL, e.g., to enable porting to an ASIC.

Control circuitry 130 may be in communication with one or more strain gauges 122, e.g., via contacts 135 which may be communicatively coupled with feed-through pins 126. In various embodiments, control circuitry 130 may be configured to convert a signal received from one or more strain gauges 122 into digital data (e.g., 16 bits) representative of the signal. Once control circuitry 130 has converted the signal from one or more strain gauges 122 into digital data, control circuitry 130 may wirelessly transmit that digital data to various remote computing devices, such as wireless readers at a doctor's office, or in the operating room. Control circuitry 130 may employ various types of communication protocols to transmit data to a wireless reader. For example, in some embodiments, control circuitry 130 may insert into a wireless data stream a 4-bit marker, a 32-bit serial number, a 16-bit strain data (converted from the signal from strain gauges 122), an 8-bit checksum and a 4-bit end marker. One or more of these data fields may or may not be encoded using various schemes. For example, the sixteen bits of strain data may be Manchester encoded, while the 4-bit markers may not necessarily be Manchester encoded. Of course, this is simply one example of how data may be organized into a wireless data stream. Other variations are possible.

Various types of antenna 138 may be contained within the second hermetically-sealed inner chamber 128. In some embodiments, antenna 138 may be spaced from control circuitry 130, e.g., by way of a frame 140. This may avoid interference between control circuitry 130 and antenna 138. Antenna 138 may come in various forms. In the embodiments depicted in the drawings, antenna 138 takes the form of a coil 142 wrapped around a portion of frame 140 that spaces coil 142 from control circuitry 130.

Figure 6:
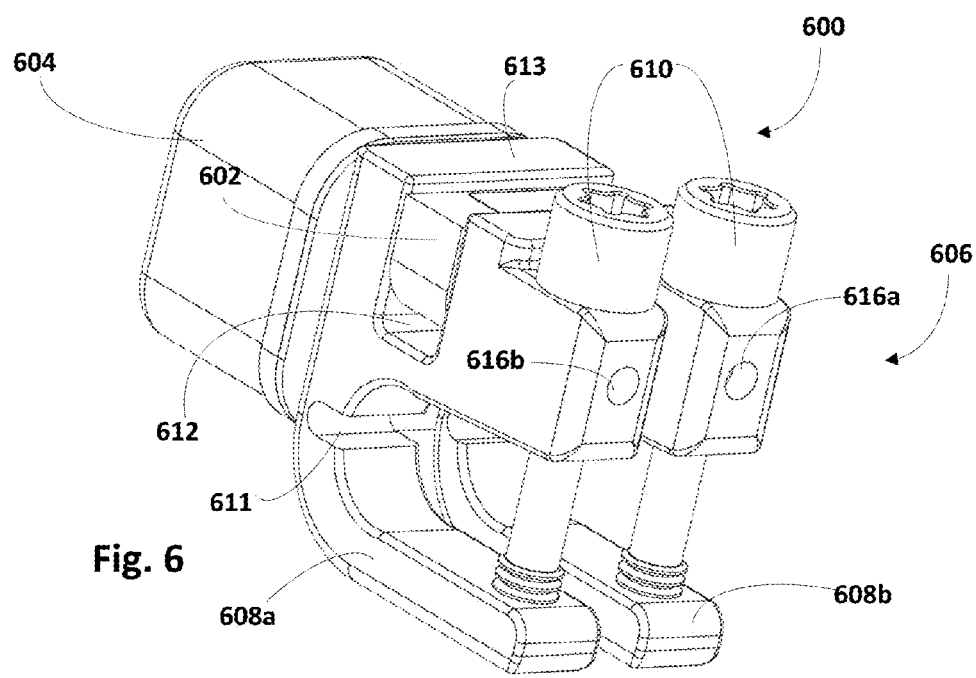
FIGS. 6 and 7 are perspective views of alternative embodiments of an implantable sensor, in accordance with various embodiments.

FIG. 6 depicts, in accordance with another embodiment, an apparatus 600 that is similar in many respects as apparatus 100 in FIG. 1, which is why many of the reference numerals are similar. However, apparatus 600 has housing 604 mounted on a side of clamping apparatus 606, rather than on platform 613. This configuration may facilitate aiming a wireless signal from an antenna (not depicted in FIG. 6) contained within housing 604 in a direction that is generally perpendicular to a direction in which a wireless signal may be transmitted from antenna 138 of apparatus 100 of FIGS. 1-3.

Figure 7:
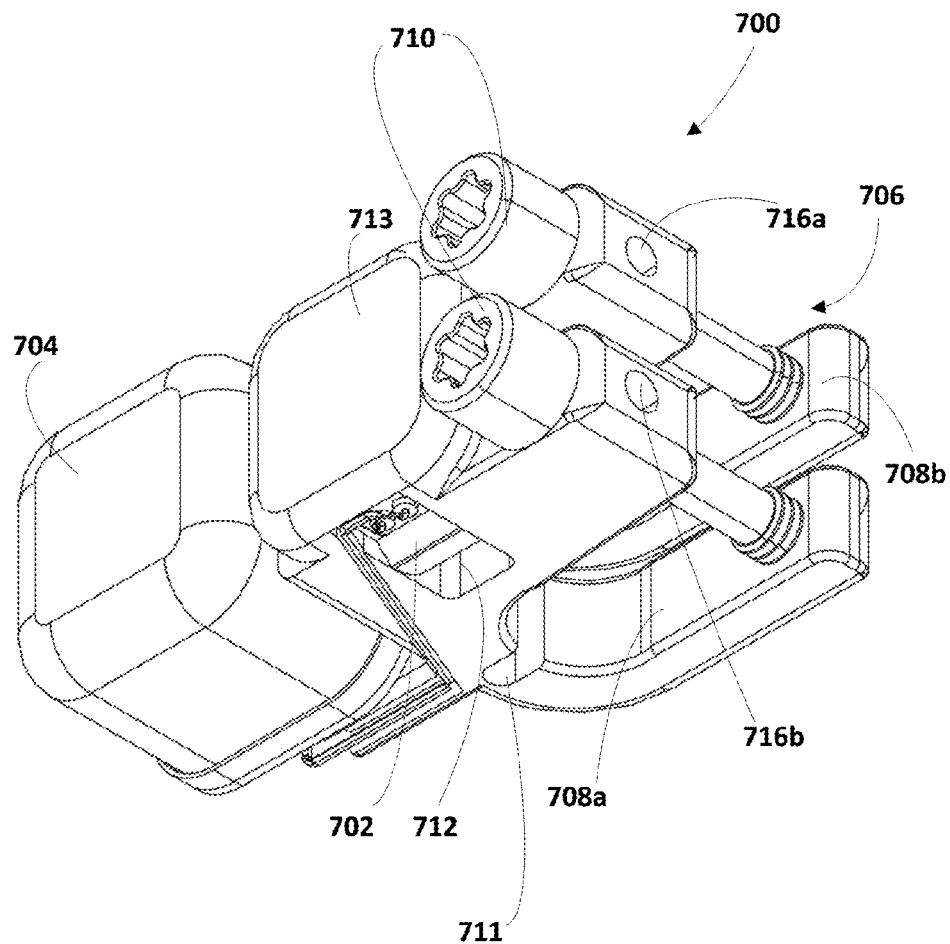

FIG. 7 depicts, in accordance with another embodiment, an apparatus 700 that is similar in many respects as apparatus 100 in FIGS. 1 and 600 in FIG. 6, which is why many of the reference numerals are similar. Like apparatus 600, apparatus 700 has housing 704 mounted to the side of clamping apparatus 706, rather than on platform 713. This configuration may have a lower profile than configurations depicted in FIGS. 1 and 6, which may be helpful where apparatus 700 is implanted permanently. As shown in FIG. 7, in some embodiments, platform 713 may span across channel 712, e.g., to protect bridge 702 from external forces.

Figure 8:
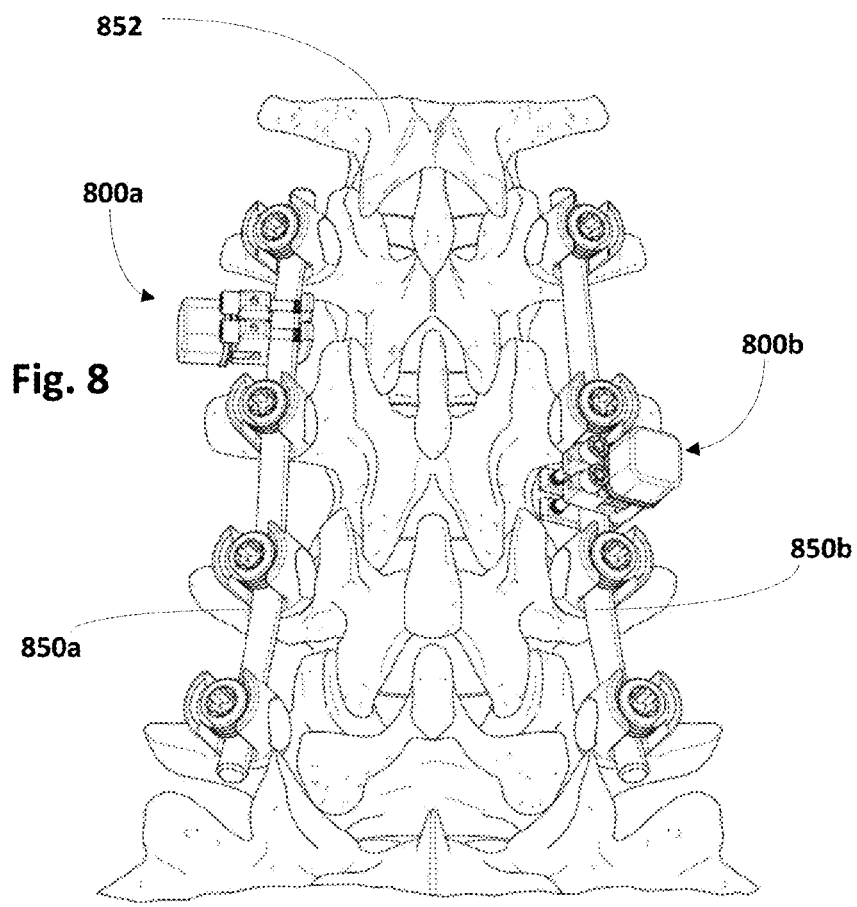
FIGS. 8-9 depict implantable sensors configured with selected aspects of the present disclosure mounted on spinal fusion rods disposed parallel to a human spine.
Figure 9:
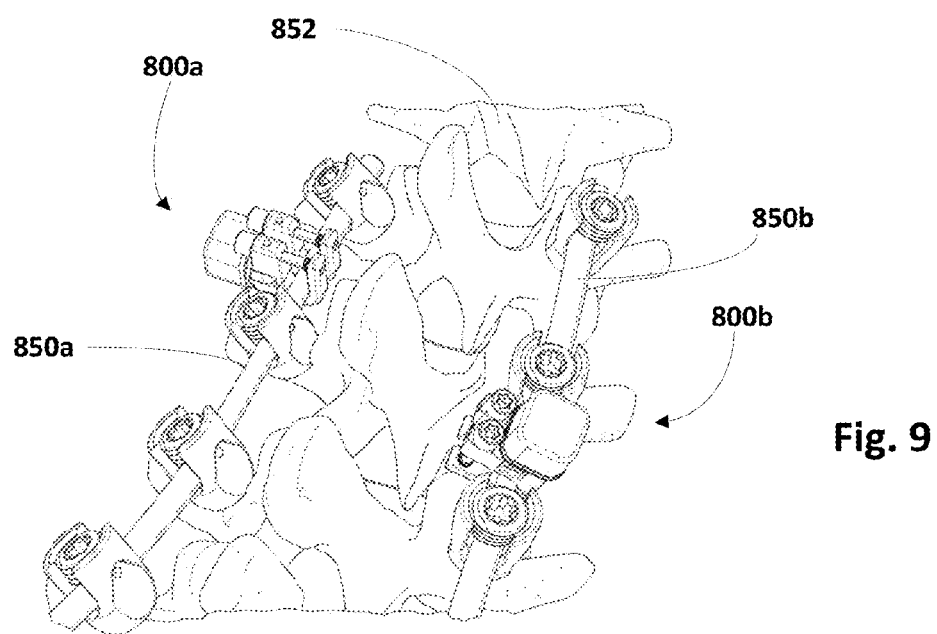

Implantable sensors such as apparatus 100, 600 and/or 700 may be used in various applications. In FIGS. 8 and 9, for instance, two spinal fusion rods 850a and 850b are depicted implanted adjacent and parallel to a human spine 852. Rods 850a and 850b may be used, for instance, to hold one more vertebra in place relative to one or more other vertebra. Holding a vertebra in place relative to another may facilitate fusion of those vertebras.

Multiple apparatus 800a and 800b configured with selected aspects of the present disclosure (e.g., 100, 600, 700) may be mounted on rods 850a and 850b, respectively, e.g., by placing each apparatus 800 so that the respective rod 850 is within clamps (e.g., 108 and 109 of FIG. 1) of the apparatus 800 when screws (e.g., 110 in FIG. 1) are tightened (see FIG. 2). Tension or strain sensed in rods 850a or 850b by apparatus 800a or 800b may be indicative of various things. For instance, a rod having too much strain may be indicative of spinal fusion not occurring between two or more vertebra. A rod with decreasing or little strain, e.g., relative to strain measured when apparatus 800a and 800b are installed (e.g., at time=0) may be indicative of two vertebras being fused.

Apparatus 800a and 800b may be oriented on rods 850a and 850b in various ways to measure various types of strain. For instance, in FIGS. 8 and 9, two apparatus 800a and 800b are depicted mounted on rods 850a and 850b, respectively, oriented approximately ninety degrees from each other. Apparatus 800a on the top left is oriented so that its housing 104 (see FIG. 1) is pointed generally to the left of spine 852. This apparatus 800a measures lateral strain of rod 850a. Lateral strain of rod 850a (e.g., left/right in FIG. 8) may be indicative of various things, such as scoliosis and/or fusion or non-fusion of two vertebra. The other apparatus 800b on the bottom right is oriented so that its housing 104 is pointed generally outward from the page. This apparatus 800b measures strain of rod 850b along a plane between the patient's front and rear. Strain in rod 850b in this plane may be indicative of various things, such as fusion or non-fusion of two vertebras.

In some embodiments where a plurality of sensors are implanted in a patient, the sensors may implement various anti-collision or collision-reduction schemes, e.g., to minimize the time necessary to obtain a reading from all of the sensors. For instance, assume x sensors are implanted in a patient. In various embodiments, each of the x sensors may be assigned a unique identifier, e.g., a serial number. Those serial numbers may be used by the sensors as seeds to generate random numbers that may then be used to determine when each sensor will transmit its reading during a time interval in which a wireless reader is present.

Assume y transmission time intervals; e.g., if y=16, each transmission time interval may be $\frac{1}{16}^{th}$ of a second. Assume also that each transmission time interval is dividable into z sub-transmission time intervals. Each of a plurality of sensors implanted in or on a patient may generate y random numbers between zero and z−1. In some embodiments, each sensor may generate the y random numbers on the fly. In some embodiments, each sensor may generate and store the y random numbers in y different memory locations. In either case, during each of the y transmission time intervals, a given sensor may transmit its reading to a nearby wireless reader during a sub-transmission time interval that corresponds to the random number between zero and z−1 that it generated for that transmission time interval.

Figure 10:
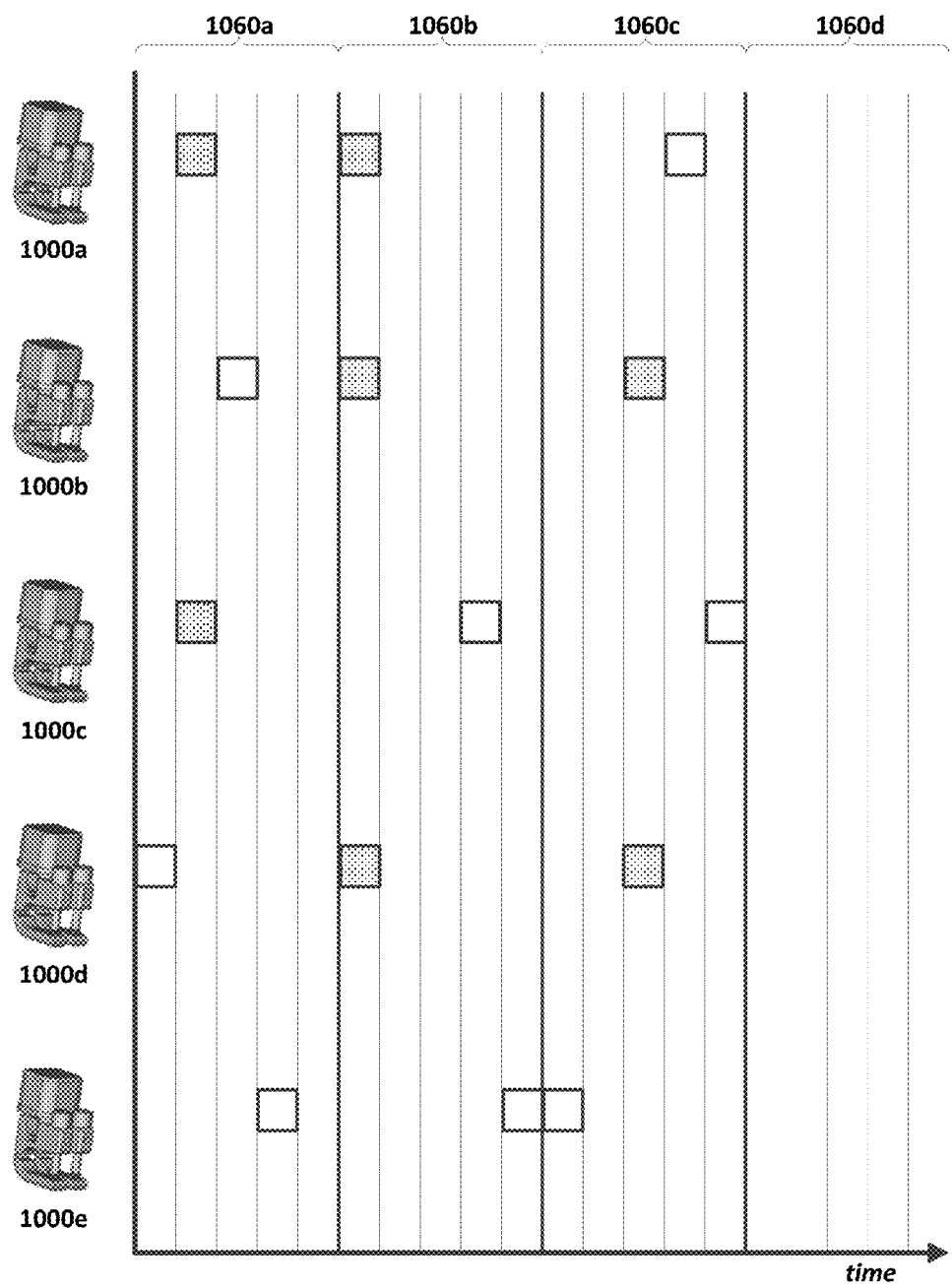
FIG. 10 depicts schematically one example communication scheme that multiple implantable wireless sensors may employ to account for collisions in data, in accordance with various embodiments.

FIG. 10 depicts an example in which five wireless sensors, 1000a-1000e (also referred to simply as "sensors"), that are implanted in an organism cooperatively communicate in this manner. The horizontal axis represents the passage of time. Assume z=5, so that random numbers generated by each implanted sensor during its designated sub-transmission time interval is in the range of 0 to 4. When a wireless reader (not depicted) is brought into wireless range of sensors 1000a-1000e, a first counter may begin counting through the transmission time intervals, which are depicted up top as 1060a-d, and so on. During each transmission time interval 1060, a second counter may count through the z=5 sub-transmission time intervals.

During the first transmission time interval 1060a, first sensor 1000a may transmit its data to the wireless reader during the second sub-transmission time interval (e.g., when the second counter reaches one). First sensor 1000a may have selected this particular sub-transmission time interval stochastically, e.g., randomly based on some sort of seed (e.g., its unique serial number). Second sensor 1000b may transmit its data to the wireless reader during the third sub-transmission time interval (also selected stochastically), e.g., when the second counter reaches two. Third sensor 1000c may transmit its data to the wireless reader during the second sub-transmission time interval, e.g., when the second counter reaches one. Because first sensor 1000a also transmits during this sub-transmission time interval, a collision occurs, as indicated by the shading. The wireless reader may detect such a collision in various ways, e.g., using a checksum, and may discard the data as corrupt or attempt to perform error correction. Fourth sensor 1000d may transmit its data to the wireless reader during the first sub-transmission time interval, e.g., while the second counter reads zero. Fifth sensor 1000e may transmit its data to the wireless reader during the fourth sub-transmission time interval, e.g., when the second counter reaches three. Thus, during the first transmission time interval 1060a, sensors 1000b, 1000d and 1000e successfully transmitted their data to the wireless reader. However, sensors 1000a and 1000c did not.

During the second transmission time interval 1060b, sensors 1000a, 1000b and 1000d all stochastically select the first sub-transmission time interval to transmit their data, causing a three-way collision. Second sensor 1000b and fourth sensor 1000d already successfully transmitted their data to the wireless reader during the previous transmission time interval 1060a, but first sensor 1000a did not. Thus, first sensor 1000a still needs to transmit its data. While third sensor 1000c failed to transmit during the previous transmission time interval (1060a), it successfully transmits its data during the fourth sub-transmission time interval of transmission time interval 1060b. Fifth sensor 1000e successfully transfers its data again during the fifth sub-transmission time interval, but since the wireless reader already received that data previously, the wireless reader may simply ignore it.

During the third transmission time interval 1060c, first sensor 1000a is at last successful, alone stochastically selecting the fourth sub-transmission time interval to transmit its data. Another collision occurs when second sensor 1000b and fourth sensor 1000d both stochastically select the third sub-transmission time interval for transmission. However, since both already successfully transmitted their data, this collision may be ignored. After third transmission time interval 1060*c*, all sensors 1000*a-e* have successfully transmitted their data to the wireless reader.

When multiple implanted sensors communicate with a wireless reader in this manner, the odds that all sensors are able to transmit readings to the reader within a relatively short period of time (e.g., one second) will be high, especially where the number of sub-transmission time intervals, $z$, is greater than the number, $x$, of sensors, e.g., five in FIG. 10. Even where $z=x$, the probability that all sensors will be able to transmit readings to the reader within an acceptable amount of time may be acceptably high.

Figure 11A:
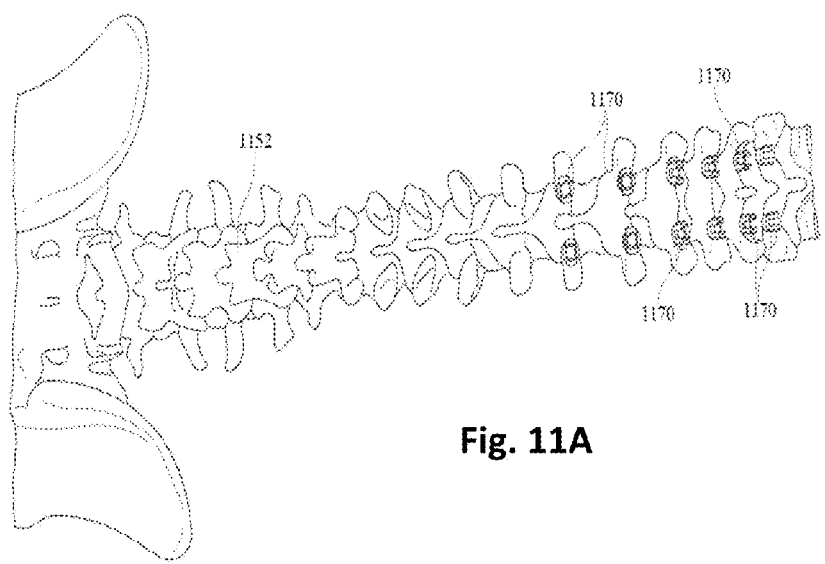
FIGS. 11A-E depict how apparatus configured with selected aspects of the present disclosure may be employed in an operation to correct kyphosis, in accordance with various embodiments.
Figure 11B:
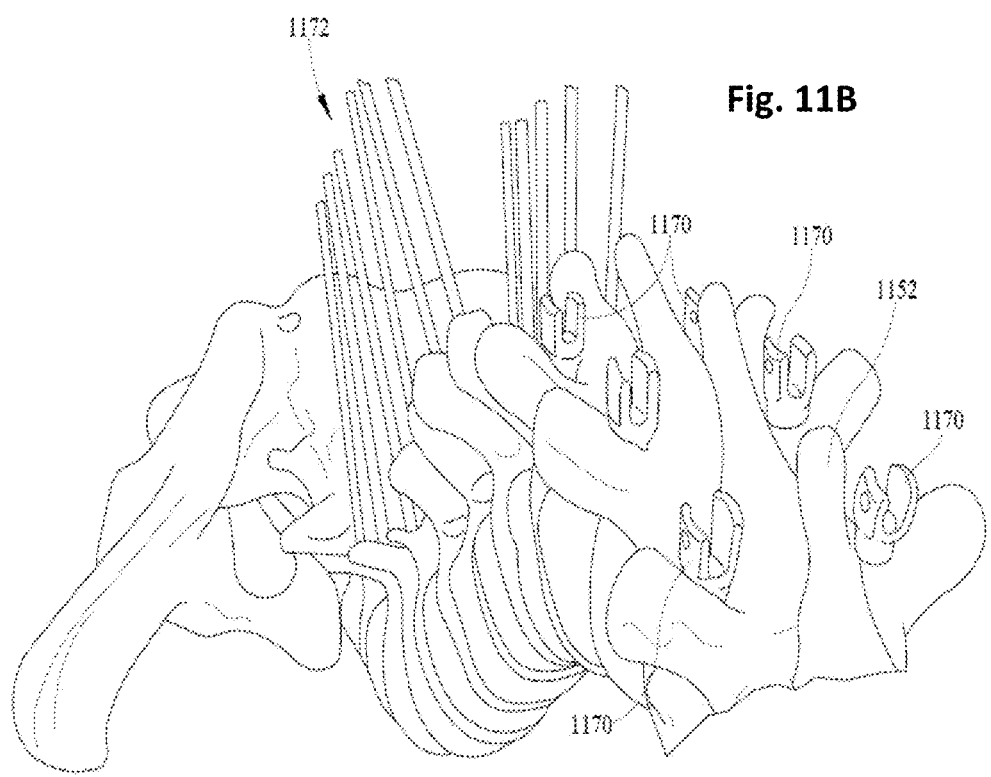

FIGS. 11A-E depict an example operation, kyphosis correction, in which apparatus 1100*a* and 1100*b* configured with selected aspects of the present disclosure (i.e., 100, 600, 700) may be employed. FIG. 11A depicts an early stage of the operation in which screws such as "tulip type" screws 1170 may be placed along an upper part (i.e., towards the patient's head) of a spine 1152, e.g., above an apex of the kyphosis. FIG. 11B depicts a stage of the operation in which a plurality of "posted" screws 1172 (e.g., screws with long threaded posts) are secured along a lower portion of spine 1152 below the apex of the kyphosis, e.g., along the lower back towards the pelvis 1174.

Figure 11C:
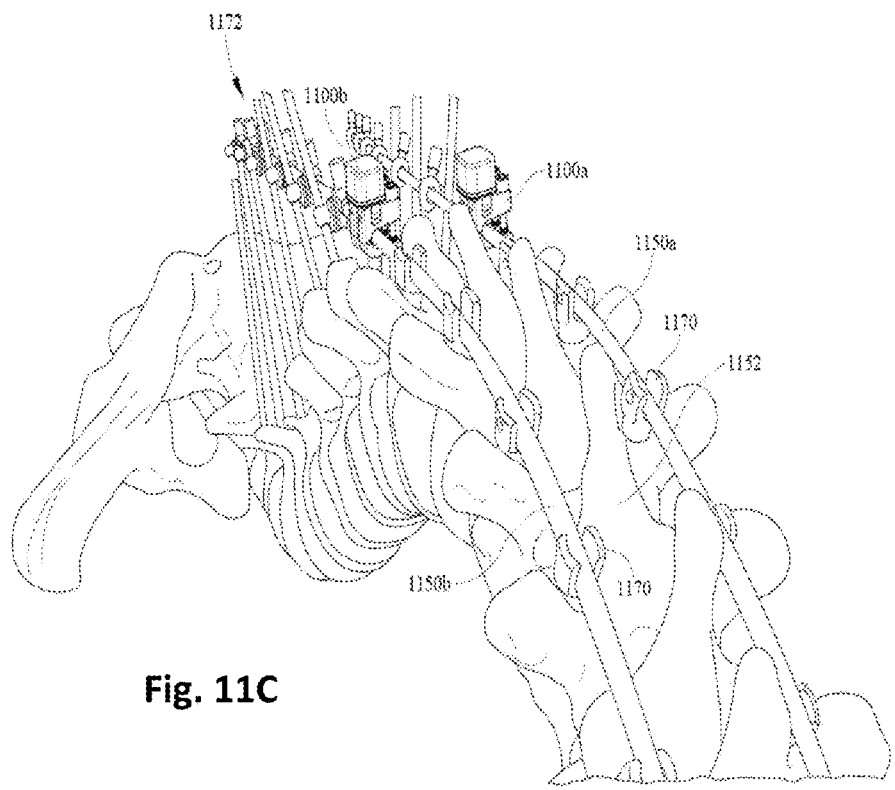
Figure 11D:
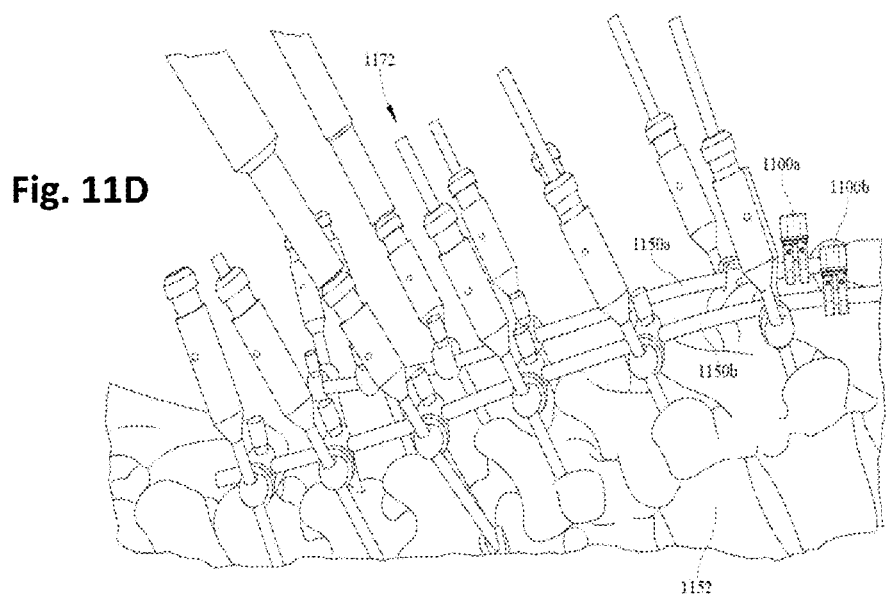
Figure 11E:
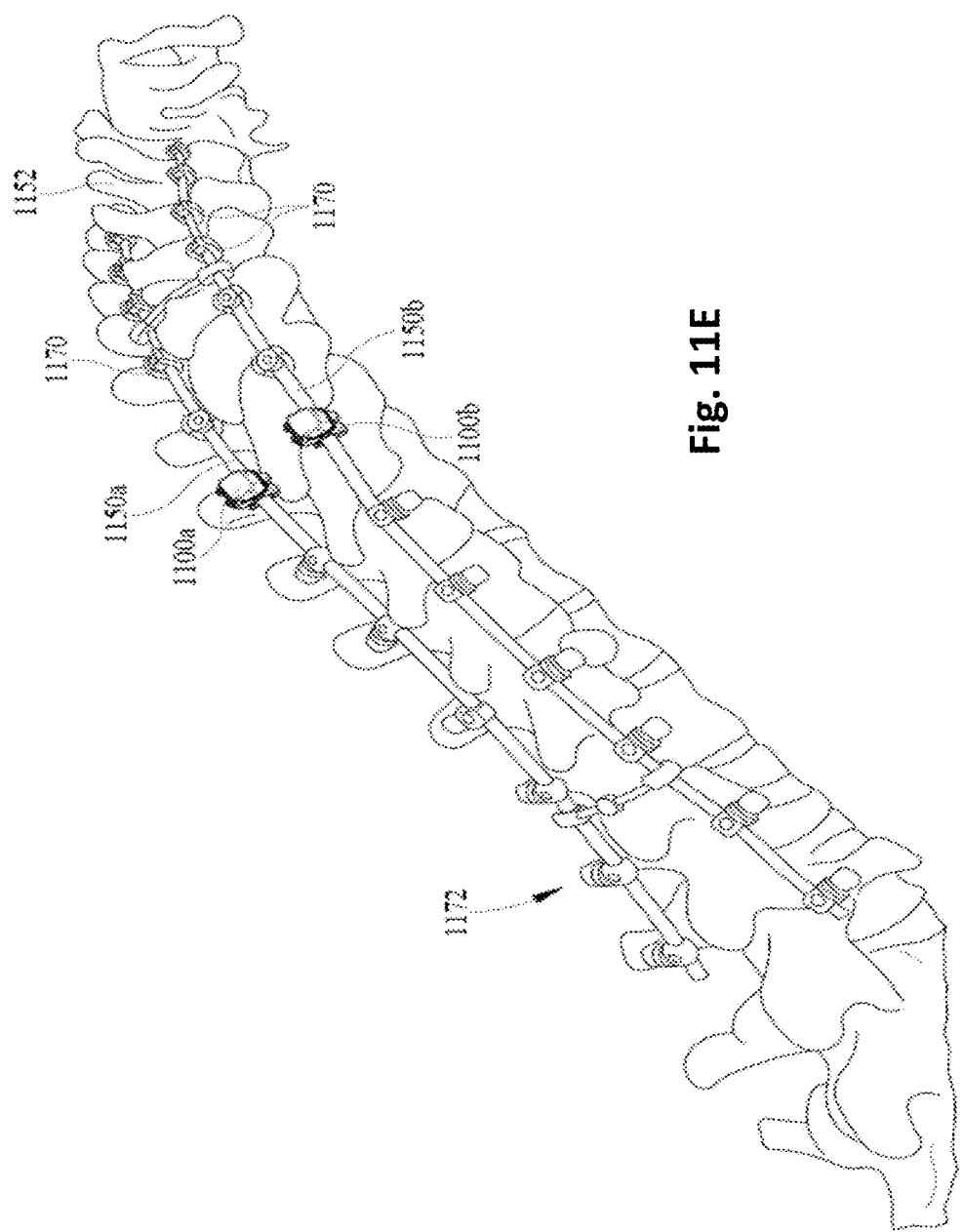

FIG. 11C depicts a stage of the operation in which fusion rods 1150*a* and 1150*b* are secured to the tulip type screws 1170 at the upper back and to the posted screws 1172 screws extending from the lower back. These threaded posted screws 1172 may be manipulated, e.g., with various drivers, to bring spinal fusion rods 1150*a* and 1150*b* closer to the lower back to straighten spine 1152. FIG. 11D depicts a stage approximately halfway through a tightening portion of the operation, in which portions of spinal fusion rods 1150*a* and 1150*b* that extend over the lower back are gradually brought closer to the lower back by tightening the posted screws 1172 in various sequences (e.g., incrementally) to minimize stress on spine 1152 and/or the various surgical components. FIG. 11E depicts a stage of the operation just before a bone graft is added, in which the posted screws 1172 have been tightened sufficiently to straighten the patient's spine 1152 considerably.

Note that in FIG. 11C, apparatus 1100*a* and 1100*b* are implanted at positions at or near the lowermost tulip type screw 1170 that is nearest the apex of the kyphosis. This may facilitate monitoring of fusion rods 1150*a* and 1150*b* for strain where it will likely be highest, particularly at the later stages of the operation depicted in FIGS. 11D and 11E. This measured strain may additionally or alternatively be compared to strains measured for any pedicle screw, e.g., in a F1717 ASTM fatigue test, e.g., to develop correlations between observed strain levels and hardware failure and/or loosening of screws.

A surgeon also may be able to use apparatus 1100*a* and 1100*b* to obtain strain measurements during the procedure, which may enable the surgeon to take remedial action. For example, the surgeon could modify the procedure to spread load over a greater number of components, or she could strive for less correction of spine 1152 to lessen strain on the various components. Additionally or alternatively, strain measurements obtained by apparatus 1100*a* and 1100*b* could be compared to each other, for example, to determine whether the loads on fusion rods 1150*a* and 1150*b* are similar.

Apparatus configured with selected aspects of the present disclosure (e.g., 100, 600, 700) may be used in other scenarios as well. For example, spinal fusion rods that are configured to be lengthened (also referred to as "growth rods") may be implanted into children or adolescents, e.g., to correct for scoliosis. Because children and adolescents grow, it may be necessary to periodically lengthen the spinal fusion rods to accommodate that growth. Rod lengthening may be performed in various ways, depending on the type of growth rod. In some instances where a growth rod must be lengthened manually, rod lengthening involves minor surgery. In other instances, noninvasive techniques may be employed. For example, some growth rods are capable of being lengthened noninvasively, e.g., using magnetism.

However growth rods are lengthened, to determine when to lengthen the rods, medical personnel typically take x-rays or wait until the patients complain of pain. However, apparatus configured with selected aspects of the present disclosure may be used instead to determine when to lengthen the rods. An apparatus such as 100, 600 or 700 may be secured to the patients' fusion rods, e.g., at the time of initial surgery. The apparatus may then be monitored as the patient grows over a period of months or years. The apparatus may show an increasing strain over time as the spine grows and the spinal fusion rods and screws resist the growth. Surgeons could use various strain benchmarks or thresholds to determine when it is time to adjust the length of the growth rods. When a benchmark or threshold is met, surgeons may perform minor surgery to lengthen the rod manually, or may use noninvasive techniques such as the magnetic rods mentioned above to adjust rod length, until the strain measured by the apparatus decreases to a desired level. Put another way, strain (which may be related to Young's modulus) may be used as feedback for initiating and/or performing rod lengthening.

Figure 12:
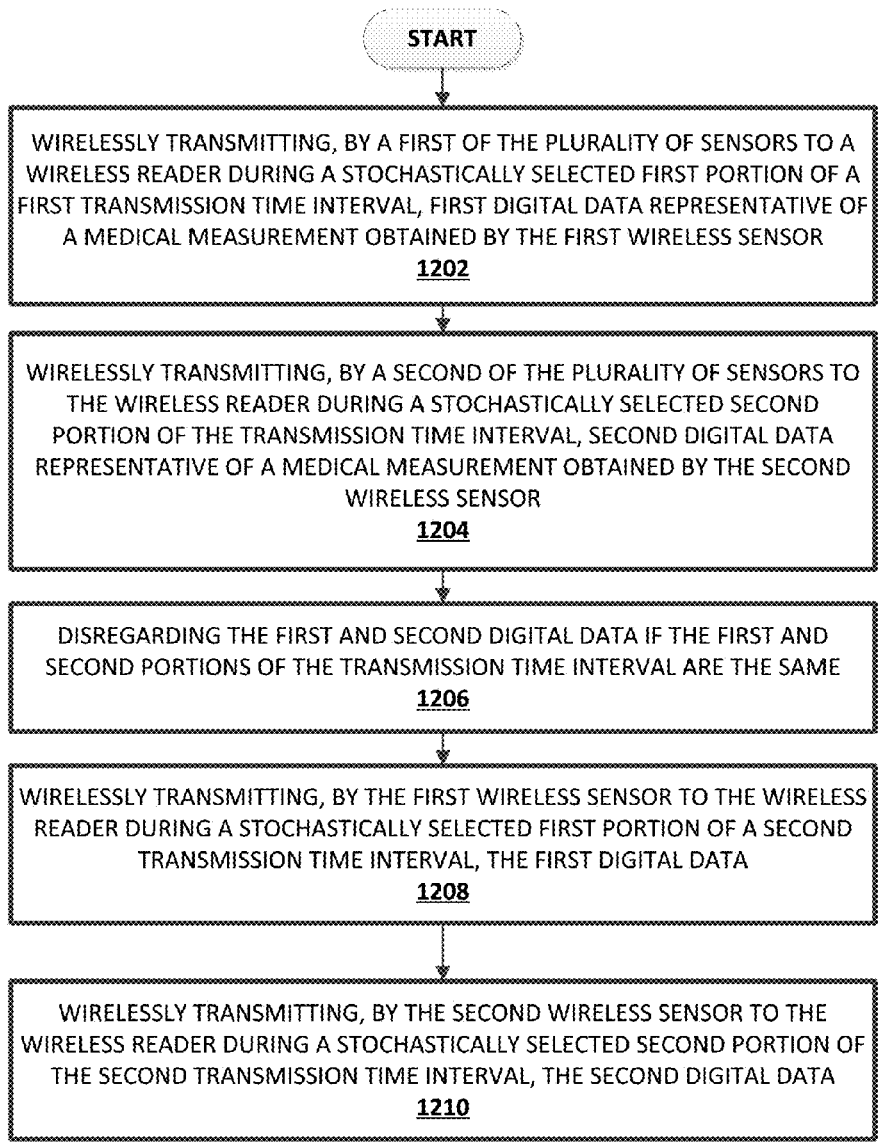
FIG. 12 depicts an example method that may be performed by implanted wireless sensors such as those depicted in FIG. 10, in accordance with various embodiments.

FIG. 12 depicts an example method 1200 that may be employed, e.g., at least in part by wireless implanted sensors such as those depicted in FIG. 10, in accordance with various embodiments. At block 1202, a first (e.g., 1000*a*) of the plurality of wireless sensors may transmit, to a wireless reader during a stochastically selected first portion of a first transmission time interval (e.g., 1060*a*), first digital data representative of a medical measurement obtained by the first wireless sensor.

At block 1204, a second (e.g., 1000*b*) of the plurality of wireless sensors may transmit, to the wireless reader during a stochastically selected second portion of the first transmission time interval, second digital data representative of a medical measurement obtained by the second wireless sensor. At block 1206, the first and second data may be disregarded, e.g., by the wireless reader, if the first and second portions of the first transmission time interval are the same (e.g., a collision).

At block 1208, the first wireless sensor may transmit, to the wireless reader during a stochastically selected first portion of a second transmission time interval (e.g., 1060*b*), the first digital data. At block 1210, the second wireless sensor may transmit, to the wireless reader during a stochastically selected second portion of the second transmission time interval, the second digital data.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A spinal implant-monitoring apparatus, comprising:
   a bridge defining a first hermetically-sealed interior and including a first leg and a second leg that extend parallel to one another and laterally from a span of the bridge;
   one or more strain gauges contained within the first hermetically-sealed interior to provide a signal indicative of strain measured at the bridge;
   a first clamp and a second clamp, the clamps being configured to be rigidly secured to a rod implanted in a patient's body, wherein each of the first and second clamp defines a respective recess into which a respective first or second leg of the bridge is inserted and secured, and wherein one or both of the clamps define a platform adjacent the respective recess;
   a housing defining a second hermetically-sealed interior, the housing mounted on the platform defined by one or both of the clamps, adjacent the bridge; and
   control circuitry contained within the second hermetically-sealed interior, the control circuitry in communication with the one or more strain gauges and configured to convert the signal into digital data representative of the signal.

2. The spinal implant-monitoring apparatus of claim 1, further comprising an antenna contained within the second hermetically-sealed interior and spaced from the control circuitry.

3. The spinal implant-monitoring apparatus of claim 2, wherein the antenna comprises a coil wrapped around a portion of a frame that spaces the coil from the control circuitry.

4. The spinal implant-monitoring apparatus of claim 2, wherein the control circuitry is configured to wirelessly transmit, to a reader via the antenna, the digital data representative of the signal.

5. The spinal implant-monitoring apparatus of claim 4, wherein the control circuitry is further configured to wirelessly transmit the digital data during a portion of a transmission time interval that is stochastically selected from a plurality of portions of the transmission time interval.

6. The spinal implant-monitoring apparatus of claim 5, wherein the transmission time interval is one of a plurality of transmission time intervals, each divided into a plurality of sub-transmission time intervals, and wherein the control circuitry is further configured to transmit the digital data during a stochastically selected sub-transmission time interval of each of the plurality of transmission time intervals.

7. The spinal implant-monitoring apparatus of claim 5, wherein the portion of the transmission time interval is stochastically selected based at least in part on a unique identifier assigned to the spinal implant-monitoring apparatus.

8. The spinal implant-monitoring apparatus of claim 1, wherein the housing comprises a generally planar lid mounted on a ceramic cap, wherein a portion of the ceramic cap adjacent the generally-planar lid is encompassed by a metal ring, wherein the metal ring is welded to a metal portion of the generally-planar lid.

9. The spinal implant-monitoring apparatus of claim 1, wherein at least one of the one or more strain gauges is communicatively coupled with an adjacent strain gauge.

10. The spinal implant-monitoring apparatus of claim 1, wherein the one or more strain gauges comprises a plurality of strain gauges connected in series to form a series of strain gauges.

11. The spinal implant-monitoring apparatus of claim 10, wherein terminal ends of the series of strain gauges are coupled with feed-through pins that pass from within the first hermetically-sealed interior to a position exterior from the bridge.

12. The spinal implant-monitoring apparatus of claim 11, wherein the feed-through pins pass through the housing into the second hermetically-sealed interior to couple the series of strain gauges with the control circuitry.

13. The spinal implant-monitoring apparatus of claim 1, wherein at least one of the two clamps includes isolation structure that is securable to the other of the two clamps to maintain a secured connection between the two clamps, wherein the secured connection isolates strain sensed by the bridge from other forces imparted on the spinal implant-monitoring apparatus.

14. The spinal implant-monitoring apparatus of claim 13, wherein the isolation structure comprises the platform.

15. The spinal implant-monitoring apparatus of claim 1, wherein the bridge comprises a stress concentration zone in a location that is separate from the hermetically sealed interior of the bridge.

* * * * *